April 16, 1957 E. B. GREGORY Plant Pat. 1,590
PYRACANTHA PLANT
Filed July 25, 1955
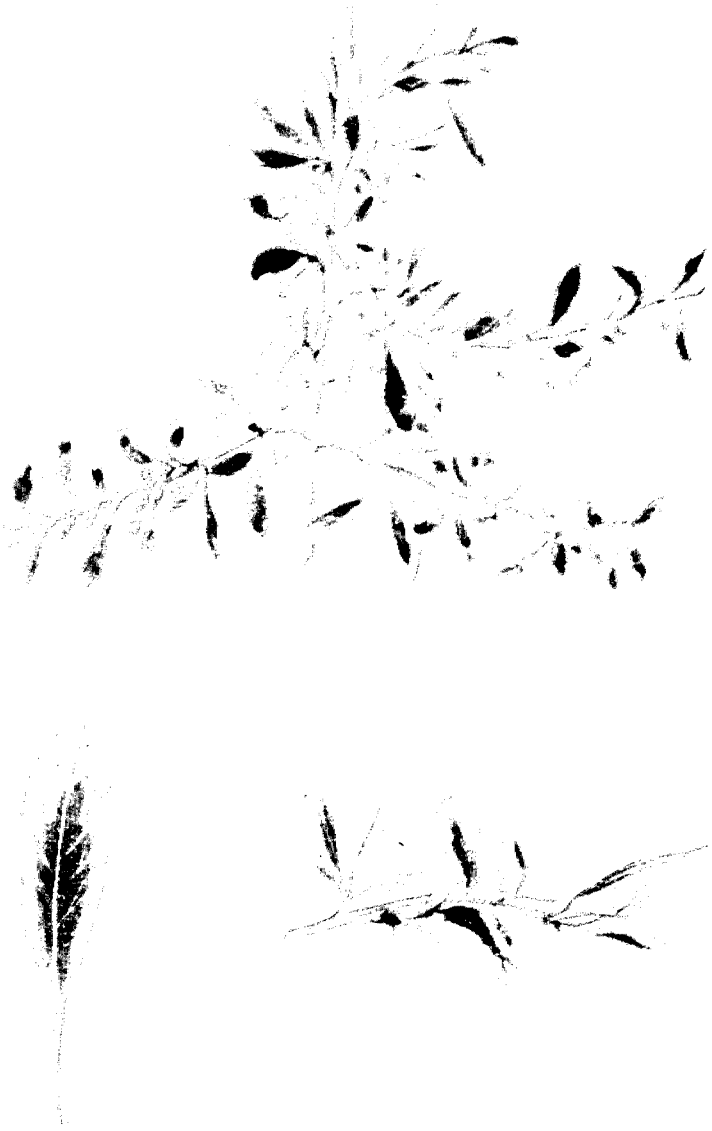
INVENTOR.
EMILY BETTS GREGORY
BY Patrick D. Wesley
ATTY.

United States Patent Office

Plant Pat. 1,590

Patented Apr. 16, 1957

1,590

PYRACANTHA PLANT

Emily Betts Gregory, Tucker, Ga.

Application July 25, 1955, Serial No. 524,314

1 Claim. (Cl. 47—59)

This disclosure relates to a new and distinct variety of Pyracantha plant belonging to the family of *Pyracantha gibbsi yunnanensis* which is an evergreen berry-bearing sort of family of plants and particularly to a new plant of this sort characterized in appearance by much smaller but more densely growing leaves on the branches and especially by the variegation of color on the leaves from dark green to an almost white.

An important feature of my plant is the unusual appearance of the leaves, especially for an evergreen.

Another primary characteristic of my plant is found in the reduced size of the leaves and in the larger number of groups and clusters of leaves on the branches, as opposed to the larger more spaced leaves on other Pyracantha plants.

A still further advantage of this plant is found in such less pronounced and less apparent characteristics in comparison with other Pyracantha as being more spreading in growth and less vigorous and in the sparse and scattered production of berries.

A plant such as I disclose here is very valuable and desirable from a commercial standpoint as an outside yard ornament and in some circumstances as an inside potted plant. The beautiful and pleasing appearance of the variegated leaves constitutes a most pleasant sight in drab winter months, alone and in the midst of conventional dark green leaved evergreen bushes, trees, and shrubs. Cuttings are readily rooted or may be kept in water for a period of time indoors and in doing so fade much slower than other Pyracantha plants' cuttings.

This plant originated with me at my nursery fields of cultivated Pyracantha on my place at Tucker, Georgia near Atlanta and is believed to be a mutation or sport from the *Pyracantha gibbsi yunnanensis,* among which it was developed. Several years of experimenting heretofore with Pyracantha and especially with this plant has proved that it is truly a distinctive plant, the characteristics of which are fixed and are not caused by or affected by the soil or sunlight-shade condition. I have propagated this plant in cultivated fields of open beds at 4600 La Vista Road, Tucker, Georgia, dozens of times by means of cuttings and all such plants produced thereby are true and have the same characteristics as the plant from which they were taken. I have rooted cuttings from the originial plant in open beds containing a mixture of equal parts of peat moss, sand, and garden soil.

The accompanying drawing accurately presents in color a fully developed, single trunk plant; a cluster of leaves on a branch of this plant; and an enlarged leaf of my plant.

*Plant characteristics*

*Leaves.*—This is one of the prime characteristics of my plant in that instead of the large, solid and dark green conventional Pyracantha leaves the present plant has leaves of variegations of greens starting generally with a dark center midrib and changing color of green toward the outer edges until at the outermost edge is an almost white or cream color apparent to the normal eye. The leaves are more or less oblanceolate in shape and there is some but slight variation from one leaf to another in the degree of variegation and in the proportion of one color of green to another. There will be on each branch a few, but very few, solid or almost solid green leaves.

The size and shape of the leaves is a distinguishing characteristic of my plant as each and every leaf when fully developed is much smaller in relative size to any other Pyracantha, fully developed plants; there are more leaves in this plant than in an equal length of branch of conventional Pyracantha and the leaves hereof tend to be in dense clusters along the twigs. It is believed that my plant can immediately and unquestionably be identified by comparison of the leaves alone.

*Berries*—At certain times of the year, just like all other Pyracantha plants, the present plant produces berries of the same general size, color, and shape of the *gibbsi yunnanensis* plants. However, the present plant's berries are not arranged in the usual clusters but are more spaced along the various branches, there are fewer of the berries, that is, the number is sparse and the berries are not found in groups of several in one location, but rather usually singly in each spot and only two or three berries in any one location.

*Growth*—The growth habit of this plant is slightly more spreading than other Pyracantha and less vigorous, and with slightly more dense branch production.

*Color*—At the leaf margin the green is A6 (Dictionary of Color, by Maerz and Paul, McGraw-Hill Book Company, 1930) darkening toward the midvein to H9 or in some leaves to J11. The brown stem varies from B7 to C9. In early spring the new growth, leaves and stems, is tinged with red B8 to C9. All "Maerz and Paul" colors.

*Size*—The plant is more spreading than *Pyracantha cocinea* and less vigorous. Its ultimate height is usually 6 feet. If uncrowded its spread will be approximately 3 feet.

*Common characteristics*

This plant has retained many of the desirable characteristics common to all known Pyracantha plants, especially like the *gibbsi yunnanensis.* It has the same composite flowers, the same color and size of berry, the same hardy resistance to both frost and drought, and the same hardiness to other environmental conditions. The flowering habit, berry production (distributed as set forth heretofore) follows the same general pattern of other Pyracantha insofar as season and longevity.

The leaves when fully matured are approximately ⅝″ in length along the medial line and around ¼″ in width at the widest point which is normally beyond the lateral center line. The leaves sharply taper at the connecting or rear portion and are more or less curved at the outer end.

I claim:

A new and distinct variety of Pyracantha plant of the hardy *gibbsi yunnanensis* class, substantially as herein shown and described, primarily characterized by its small leaves with definite variegations of green to light cream or white with the habit of an evergreen plant, said leaves being oblanceolate in form with a dark green at the center and variegating toward the outer edges, its leaves being in dense clusters along the small branches, and having the usual red berries being more sparse, the unusual color of the leaves being the prime characteristic and the size and plurality of the leaves also an outstanding characteristic, none of which are substantially affected by sunlight or soil or shade or fertility conditions.

No References Cited.